(12) United States Patent
Murase et al.

(10) Patent No.: US 8,709,472 B1
(45) Date of Patent: Apr. 29, 2014

(54) BIOACTIVE AGENT-LOADED HEART-TARGETING NANOPARTICLES

(75) Inventors: Katsuyuki Murase, Cupertino, CA (US); Florian Ludwig, Mountain View, CA (US); Dariush Davalian, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1631 days.

(21) Appl. No.: 11/939,487

(22) Filed: Nov. 13, 2007

(51) Int. Cl.
*A61K 47/42* (2006.01)
*A61K 47/48* (2006.01)

(52) U.S. Cl.
USPC ............ 424/450; 424/1.69; 514/1.1; 514/773

(58) Field of Classification Search
USPC .................. 424/450, 1.69, 489, 9.36, 9.1
See application file for complete search history.

(56) References Cited

U.S. PATENT DOCUMENTS

| | | | |
|---|---|---|---|
| 6,117,632 A * | 9/2000 | O'Mahony | 435/6 |
| 6,168,804 B1 | 1/2001 | Samuel et al. | |
| 6,258,378 B1 | 7/2001 | Schneider | |
| 6,451,338 B1 | 9/2002 | Gregoriadis et al. | |
| 7,439,041 B2 * | 10/2008 | Michelitsch et al. | 435/69.3 |
| 7,501,486 B2 * | 3/2009 | Zhang et al. | 530/330 |
| 2006/0160743 A1 | 7/2006 | Zhang et al. | |

FOREIGN PATENT DOCUMENTS

WO  WO99/58694 A1 * 11/1999

OTHER PUBLICATIONS

Teruyuki et al., "Development and applications of nano-scale biocompatible anchor for cell membrane", Fragr. J. vol. 31, No. 8, pp. 81-86 (2003) (enclosed English Abstract only).*
Teruyuki et al., "Development and applications of nano-scale biocompatible anchor for cell membrane", Fragr J. vol. 31, No. 8, pp. 81-86 (2003) (enclosed English Abstract only).
Kato et al., "Rapid Protein Anchoring into the Membranes of Mammalian Cells Using Oleyl Chain and Poly(ethylene glycol) Derivatives", Biotech. Prog. 20 (3), pp. 897-904 (2004).
Kato et al., "Immobilized culture of nonadherent cells on an oley poly(ethylene glycol) ether-modified surface", BioTechniques vol. 35, No. 5, pp. 1014-1021 (2003).
Zhang et al., "Molecular Profiling of Heart Endothelial Cells", Circulation vol. 112, No. 11, pp. 1601-1611 (2005).
Cell Immobilization, Micro Array, Cell Membrane Modifier, downloaded Feb. 27, 2007 from www.nof.co.jp/english/business/dds/bam/con03, 7 pgs.

\* cited by examiner

*Primary Examiner* — Janet Epps-Smith
(74) *Attorney, Agent, or Firm* — Squire Sanders (US) LLP

(57) ABSTRACT

Compositions that contain bioactive agent-loaded nanoparticles with heart targeting capabilities and methods of using the same for the treatment of disease are disclosed.

15 Claims, 1 Drawing Sheet

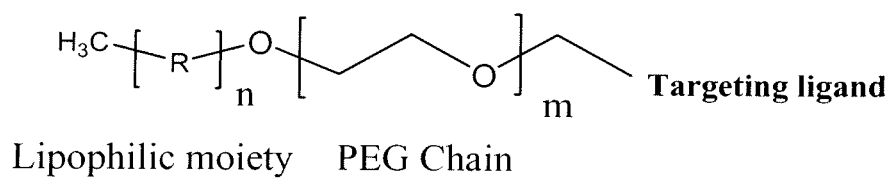
Lipophilic moiety    PEG Chain
R = saturated or unsatuated carbon chain with/without branch(es)

BIOACTIVE AGENT-LOADED HEART-TARGETING NANOPARTICLES

FIELD OF THE INVENTION

The present invention relates to bioactive agent-loaded nanoparticle compositions with surface-expressed heart targeting peptides, and methods of using the compositions for treating vascular disease.

BACKGROUND OF THE INVENTION

In healthy hearts, vessel walls are composed of an endothelial cell lining, a medial layer of vascular smooth muscle cells and an over layer of connective tissue. The endothelial cell lining is ideally situated at the interface between the blood and the vessel wall to transduce signals, with endothelial cells controlling the homeostatic balance of the vessel through the production of factors regulating processes such as vessel tone, coagulation state, cell growth, cell death, and leukocyte trafficking. Vascular smooth muscle cells maintain the contractile tone of the blood vessel in response to vasoactive agents, and release cytokines and other growth factors. In conjunction with fibroblasts, the smooth muscle cells produce extracellular matrix proteins and proteases that determine vessel structure. Occlusive vascular disease, the most common form of which is atherosclerosis, is characterized by an abnormal accumulation of lipid, inflammatory cells, vascular smooth muscle cells and extracellular matrix proteins within the intimal space between the endothelial lining and the medial layer (plaque formation).

Therapies for atherosclerosis generally prevent, arrest or reverse the process of plaque formation or stimulate the formation of new blood vessels. It is rare, however, that a drug or other agent for treatment of atherosclerosis targets only coronary vessels. More commonly, systemic administration results in undesirable side effects due, for example, to generalized toxic effects throughout the entire body. Indeed, side effects can limit the utility of existing pro-angiogenic therapies for treatment of vascular disease.

As the cells which make up the internal lining of blood vessels, endothelial cells are the first cell type encountered by a circulating drug or other substance. Endothelial cells therefore provide an excellent target for selectively directing a therapeutic substance to cardiac tissue. Indeed, such selective targeting of a therapeutic substance to heart vasculature would reduce or eliminate the risk of unwanted side effects such as systemic toxicity or malignant transformation. Selective targeting would also cause a high local concentration of the substance, thereby reducing the dosage required for effective treatment. There is therefore, a need for treatments using such selective targeting.

The present invention provides a nanoparticle composition able to selectively target cardiac vasculature and methods of using such a composition for treating a vascular disease.

SUMMARY OF THE INVENTION

The present invention relates to a composition that includes a plurality of nanoparticles, a bioactive agent encapsulated within, adhered to a surface of or integrated into the structure of the nanoparticle, a peptide group including a cysteine-arginine-proline-proline-arginine polypeptide, a peptidomimetic thereof or a homolog thereof and a lipophilic moiety attached to the peptide group, wherein the lipophilic moiety is inserted into the nanoparticle membrane to anchor the peptide group to the nanoparticle.

In various aspects, the peptide group has binding affinity for heart vein cells, heart capillary cells, heart artery cells or heart endothelial cells.

In various aspects, the lipophilic moiety includes an oleyl group.

In various aspects, a poly(ethylene glycol) (PEG) group connects the lipophilic moiety to the peptide group.

In various aspects, the PEG group comprises less than 100 ethylene glycol repeats, less than 75 ethylene glycol repeats, less than 50 ethylene glycol repeats or less than 25 ethylene glycol repeats.

In various aspects, the peptide group includes more than one cysteine-arginine-proline-proline-arginine polypeptide where each polypeptide is linked to another polypeptide by aminohexanoic acid.

In various aspects, the bioactive agent is selected from a group that includes an anti-stenosis agent, an anti-inflammatory agent, an antiplatelet, an anticoagulant, an antifibrin, an antithrombin, a cardioprotective agent, a cholesterol-lowering agent, aspirin, an angiotensin-converting enzyme, a beta blocker, a calcium channel blocker, nitroglycerin, a long-acting nitrate, a glycoprotein IIb-IIIa inhibitor or any combination thereof.

In various aspects, the composition further includes a PEG group operatively coupled to the surface of the nanoparticle.

In various aspects, the nanoparticle can be a liposome, a polymersome or a polymer particle.

Another aspect of the present invention relates to a method for treating or preventing a disease involving providing a composition according to the invention and administering a therapeutically effective amount of the composition to a patient in need thereof.

In various aspects, the disease is a vascular disease selected from the group consisting of atherosclerosis, stenosis, vulnerable plaque and heart failure.

In various aspects, administering the composition involves intraarterial delivery which can involve percutaneous transluminal coronary arterial delivery or using a catheter.

Another aspect of the invention relates to a heart targeting molecule that includes a peptide group comprising a cysteine-arginine-proline-proline-arginine polypeptide, a peptidomimetic thereof or a homolog thereof and a lipophilic moiety attached to the peptide group.

In various aspects, the lipophilic moiety includes an oleyl group.

In various aspects, the peptide group has binding affinity for heart vein cells, heart capillary cells, heart artery cells or heart endothelial cells.

In various aspects, a PEG group connects the lipophilic moiety to the peptide group.

In various aspects, the lipophilic moiety includes an amphiphilic block copolymer.

In various aspects, the peptide group includes more than one cysteine-arginine-proline-proline-arginine polypeptide where each polypeptide is linked to another polypeptide by aminohexanoic acid.

BRIEF DESCRIPTION OF THE DRAWINGS

FIG. 1 depicts a targeting ligand linked to a liphiphilic moiety via a poly(ethylene glycol) chain. The number of PEG units is designated by m and the number of lipophilic moiety units is designated by n.

DETAILED DESCRIPTION OF THE INVENTION

In many instances, localized intravascular administration of therapeutic agents would comprise a significant improvement in the art. But there are special considerations that must be taken into account in the development of a localized, intravascular therapeutic agent-delivery system. For example, the system should not promote clotting or thrombogenesis. Moreover, the system should take into account the fact that constant blood flow through the vasculature results in rapid dilution of the therapeutic agent. The present invention mitigates these issues by providing a composition that preferentially localizes to the heart vasculature.

The present invention relates to a composition that includes a plurality of nanoparticles, a bioactive agent encapsulated within, adhered to a surface of or integrated into the structure of the nanoparticles, a peptide group including a cysteine-arginine-proline-proline-arginine polypeptide, a peptidomimetic thereof or a homolog thereof and a lipophilic moiety attached to the peptide group, wherein the lipophilic moiety is inserted into the nanoparticle membrane to anchor the peptide group to the nanoparticle.

As used herein, "nanoparticle" refers to a microscopic particle, composed of one or more polymers, whose size in nanometers (nm) includes a maximum linear dimension of less than 1000 nanometers. As used herein, linear dimension refers to the distance between any two points on a nanoparticle as measured in a straight line. Nanoparticles of the present invention can be irregular, oblong, spindle, rod, discoid, pancake, cylindrical, red blood cell-like, spherical or substantially spherical in shape as long as their shape and size allow binding interactions.

As used herein, "substantially spherical" refers to a shape that is not perfectly spherical but has a generally spherical shape, e.g., an ellipsoid.

As used herein, a "polymer" refers to a molecule(s) composed of a plurality of repeating structural units connected by chemical bonds.

Several types and configurations of nanoparticles are encompassed by the present invention and may be composed of a range of materials including, but not limited to, a biostable polymer, a biodegradable polymer, fullerenes, lipids, or a combination thereof. Biostable refers to polymers that are not degraded in vivo. Biodegradable refers to polymers that are capable of being disposed of after delivery to a disease locale in a patient, e.g., when exposed to bodily fluids such as blood, and can be gradually absorbed and/or eliminated by the body.

Nanoparticles of the present invention can include biodegradable materials that, after delivery, biodegrade or bioerode within 1.0 second to 100 hours, within 10.0 seconds to 10 hours or within 1 minute to 1 hour. Methods of forming nanoparticles with known degradation rates are known to those skilled in the art; see for example U.S. Pat. No. 6,451,338 to Gregoriadis et al., U.S. Pat. No. 6,168,804 to Samuel et al. and U.S. Pat. No. 6,258,378 to Schneider et al., which are hereby incorporated by reference in their entirety.

Nanoparticles of the invention include liposomes, polymersomes and polymer particles.

As used herein, "liposome" refers to a compartment that is completely enclosed by a bilayer typically composed of phospholipids. Liposomes can be prepared according to standard techniques known to those skilled in the art. For example, without limitation, suspending a suitable lipid, e.g., phosphatidyl choline, in an aqueous medium followed by sonication of the mixture will result in the formation of liposomes. Alternatively, rapidly mixing a solution of lipid in ethanol-water, for example, by injecting a lipid through a needle into an agitated ethanol-water solution can form lipid vessicles. Liposomes can also be composed of other amphiphilic substances, e.g., shingomyelin or lipids containing poly(ethylene glycol) (PEG).

As used herein, "polymersome" refers to di- or tri-block copolymers that are modified to form bilayer structures similar to liposomes. Depending on the length and composition of the polymers in the block copolymer, polymersomes can be substantially more robust that liposomes. In addition, the ability to control the chemistry of each block of the block copolymer permits tuning of the polymersome's composition to fit the desired application. For example, membrane thickness, i.e., the thickness of the bilayer structure, can be controlled by varying the chain length of the individual blocks. Adjusting the glass transition temperatures of the blocks will affect the fluidity and therefore the permeability of the membrane. Even the mechanism of agent release can be modified by altering the nature of the polymers.

Polymersomes can be prepared by dissolving the copolymer in an organic solvent, applying the solution to a vessel surface, and then removing the solvent, which leaves a film of the copolymer on the vessel wall. The film is then hydrated to form polymersomes. Dissolving the block copolymer in a solvent and then adding a weak solvent for one of the blocks, will also create polymersomes. Other means of preparing polymersomes are known to those skilled in the art and are within the scope of this invention.

Polymersomes can be used to encapsulate bioactive agents, examples of which are described more fully below, by including the bioactive agent in the water used to rehydrate the copolymer film. Osmotically driving the bioactive agent into the core of preformed polymersomes, a process known as force loading, may also be employed. Using a double emulsion technique, polymersomes of relative monodispersivity and high loading efficiency are possible. The technique involves using microfluidic technology to generate double emulsions comprising water droplets surrounded by a layer of organic solvent. These droplet-in-a-drop structures are then dispersed in a continuous water phase. The block copolymer is dissolved in the organic solvent and self-assembles into proto-polymersomes on the concentric interfaces of the double emulsion. Completely evaporating the organic solvent from the shell yields the actual polymersomes. This procedure allows fine control over the polymersome size. In addition, the ability to maintain complete separation of the internal fluids from the external fluid throughout the process allows extremely efficient encapsulation.

As used herein, a "polymer particle" refers to a solid or porous particle, in contrast to the shell structure of liposomes and polymersomes. Methods for adhering a bioactive agent to the surface of or integrating a bioactive agent into the structure of a polymer particle are known to those skilled in the art.

Polymers that may be used to prepare nanoparticles of this invention include, but are not limited to, poly(N-acetylglucosamine) (Chitin), Chitosan, poly(3-hydroxyvalerate), poly (lactide-co-glycolide), poly(3-hydroxybutyrate), poly(4-hydroxybutyrate), poly(3-hydroxybutyrate-co-3-hydroxyvalerate), polyorthoester, polyanhydride, poly (glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly (glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrin glue, fibrinogen, cellulose, starch, collagen and hyaluronic acid, elastin and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates including tyrosine-based polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

A nanoparticle of the invention includes a peptide group anchored to the nanoparticle by a lipophilic moiety.

As used herein, "lipophilic moiety" refers to a nonpolar molecular component that can insert itself or part of itself into a nanoparticle layer of the invention. A presently preferred lipophilic moiety is an oleyl chain.

A peptide group of the invention includes a cysteine-arginine-proline-proline-arginine (CRPPR) polypeptide, a peptidomimetic thereof or a homolog thereof. In some embodiments, the peptide group includes more than one CRPPR polypeptide, where each CRPPR polypeptide can be linked together by aminohexanoic acid. It is to be understood that any number of CRPPR polypeptides can be linked together by aminohexanoic acid, methods of which are known to those skilled in the art and are encompassed by the present invention, As used herein, "peptidomimetic" refers to a small protein-like chain designed to function like a peptide. Peptidomimetics that can functionally mimic a CRPPR group are obtainable using methods known to those skilled in the art.

As used herein, "homolog" refers to a structurally related peptide group derived from a common peptide. Methods of obtaining CRPPR homologs are known to those skilled in the art.

The CRPPR polypeptide has binding affinity for heart vein cells, heart capillary cells, heart artery cells and heart endothelial cells. Specifically, CRPPR binds to the heart-expressed proteins CRIP2, Sigirr, MpcII-3 and bc10. The present invention takes advantage of these binding properties to selectively deliver bioactive agent-containing nanoparticles to the heart vasculature.

The CRPPR polypeptide, peptidomimetic or homolog thereof, is anchored to the nanoparticle by a lipophilic moiety that can include an oleyl group and additionally a poly(ethylene glycol) (PEG) group that connects the lipophilic moiety to the peptide group, as depicted in FIG. 1. It is to be understood that the targeting ligand of FIG. 1 includes a CRPPR polypeptide of the invention. It is the lipophilic nature of the oleyl group that allows it to insert into the nanoparticle membrane layer. Methods of attaching a PEG group to a lipophilic moiety and a polypeptide are known to those skilled in the art.

In various aspects, the PEG group includes less than 100 ethylene glycol repeats, i.e., n<100, less than 75 ethylene glycol repeats, less than 50 ethylene glycol repeats or less than 25 ethylene glycol repeats.

In various aspects, a nanoparticle of the invention will have one or more bioactive agents encapsulated within, adhered to a surface of or integrated into the structure of the nanoparticle.

As used herein, "encapsulated within" means the agent is contained within the space defined by the outer layer of the nanoparticle.

As used herein, "adhered to the surface of" means the agent is covalently or non-covalently attached to the outer surface of the nanoparticle.

As used herein, "integrated into the structure of" means the agent is part of the chemical structure of the material forming the nanoparticle.

Methods of encapsulating within, adhering to the surface of and integrating into the structure of are known to those skilled in the art.

Presently preferred bioactive agents, also referred to herein as therapeutic agents, include an anti-stenosis agent, an anti-inflammatory agent, an antiplatelet, an anticoagulant, an antifibrin, an antithrombin, a cardioprotective agent, a cholesterol-lowering agent, aspirin, an angiotensin-converting enzyme, a beta blocker, a calcium channel blocker, nitroglycerin, a long-acting nitrate, a glycoprotein IIb-IIIa inhibitor or any combination thereof.

Examples of anti-inflammatory agents include both steroidal and non-steroidal (NSAID) anti-inflammatory agents such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecrolimus and derivatives, analogs, prodrugs, codrugs and combinations of any of the foregoing.

Examples of antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä, calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide or nitric oxide donors, super oxide dismutases, super oxide dismutase mimetic, 4-amino-2,2,6,6-tetramethylpiperidine-1-oxyl (4-amino-TEMPO) and derivatives, analogs, prodrugs, codrugs and combinations thereof.

Examples of other bioactive agents include, without limitation, actinomycins, taxol, docetaxel, paclitaxel, rapamycin, 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, everolimus, biolimus, zotarolimus, perfenidone and derivatives, analogs, prodrugs, co-drugs and combinations of any of the foregoing.

In certain aspects of the invention, nanoparticles can further include a PEG group operatively coupled to the surface of the nanoparticle independent of the CRPPR peptide group.

As used herein, "operatively coupled' refers to the attachment of a PEG group to the surface of a nanoparticle through either direct or indirect means. For example, it is possible for the PEG group to directly attach to the nanoparticle surface by a portion of the PEG group itself. Alternatively, it is possible for the PEG group to be attached to the surface of the nanoparticle via an intermediate component that couples the PEG group to the nanoparticle surface, e.g., an oleyl group. Exemplary intermediate components are known to those skilled in the art and are encompassed by the present invention.

Nanoparticles with PEG on their surface have an increased ability to evade detection by a host's immune system over nanoparticles without PEG on their surface. This increased ability allows PEG-modified nanoparticles more time to move through the vasculature, thereby allowing the CRPPR peptide group more time to selectively target heart vein cells, heart capillary cells, heart artery cells or heart endothelial cells such as coronary artery endothelial cells.

Another aspect of the present invention relates to a method for treating or preventing a disease involving providing a composition according to the invention and administering a therapeutically effective amount of the composition to a patient in need thereof. Administering the composition can involve intraarterial delivery including percutaneous transluminal coronary arterial delivery or using a catheter. Vascular diseases that may be treated by this method include, but are not limited to, atherosclerosis, stenosis, vulnerable plaque and heart failure.

As used herein, "treating" refers to the administration of a therapeutically effective amount of a bioactive agent to a patient known or suspected to be suffering from a vascular disease.

As used herein, "therapeutically effective amount" refers to the amount of bioactive agent that has a beneficial effect, which may be curative or palliative, on the health and well-being of a patient with regard to a disease with which the patient is known or suspected to be afflicted. A therapeutically effective amount may be administered as a single bolus, as intermittent bolus charges, as short, medium or long term sustained release formulations or as any combination of these.

As used herein, "known" to be afflicted with a disease refers first to a condition that is relatively readily observable and/or diagnosable. An example, without limitation, of such a disease is atherosclerosis, which is a discrete narrowing of a patient's arteries.

As used herein, "vascular disease locale" refers to the location within a patient's body where an atherosclerotic lesion(s) is present, where stenosis may develop or the site of vulnerable plaque(s).

An atherosclerotic lesion refers to a deposit of fatty substances, cholesterol, cellular waste products, calcium and/or fibrin on the inner lining or intima of an artery.

Stenosis refers to the narrowing or blockage of an artery.

Vulnerable plaque on the other hand is quite different from either atherosclerosis or stenosis and would generally come under the designation "suspected" affliction. This is because vulnerable plaque occurs primarily within the wall of a vessel and does not cause prominent protrusions into the lumen of the vessel. It is often not until it is "too late," i.e., until after a vulnerable plaque has broken and released its components into the vessel, that its presence is even known. Numerous methods have and are being investigated for the early diagnosis of vulnerable plaque but to date none have proven completely successful. Thus, the regional treatment of a segment of a vessel suspected of being afflicted with vulnerable plaque may be the best way to address such lesions.

As used herein, "bioactive agent" refers to any substance that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to retrogress; or (4) alleviating one or more symptoms of the disease.

As used herein, a bioactive agent also includes any substance that has a prophylactic beneficial effect on the health and well-being of the patient, when administered to a patient known or suspected of being particularly susceptible to a disease. A prophylactic beneficial effect includes, but is not limited to: (1) preventing or delaying on-set of a disease; (2) maintaining a disease at a retrogressed level once such level has been achieved by a therapeutically effective amount of a therapeutic agent, which may be the same as or different from the therapeutic agent used in a prophylactically effective amount; or (3) preventing or delaying recurrence of a disease after a course of treatment with a therapeutically effective amount of a therapeutic agent, which may be the same as or different from the therapeutic agent used in a prophylactically effective amount.

The amount of bioactive agent in a nanoparticle will depend on the required minimum effective concentration (MEC) of the agent and the length of time over which it is desired that the MEC be maintained. For most therapeutic agents the MEC will be known, or readily derivable by those skilled in the art from the literature. For experimental bioactive agents or those for which the MEC by localized delivery is not known, such can be empirically determined using techniques well-known to those skilled in the art.

It is to be understood that once nanoparticles are selectively targeted to the vasculature, they can degrade to release the bioactive agent. In addition, nanoparticles of the invention can possess triggered release capabilities. For example, thermo-, ultrasound-, light- or other-sensitive bioactive agent-loaded nanoparticles can be used. Once the nanoparticles are located at a vascular disease locale, the nanoparticles can be triggered to release the bioactive agent by heating, light activation, or ultrasound. This may be done locally through a catheter-based intervention, e.g., heat or light, by an external device able to localize heat within a body, e.g., focused microwave radiation, or globally, e.g., by inducing fever or by ultrasound triggering, although in this latter case, the bioactive agent would still be localized by localization of the drug carrier.

Another aspect of the invention relates to heart targeting molecules that include a peptide group comprising a cysteine-arginine-proline-proline-arginine polypeptide, a peptidomimetic thereof or a homolog thereof and a lipophilic moiety attached to the peptide group. The lipophilic moiety can include an oleyl group.

In other embodiments, the lipophilic moiety can include an amphiphilic block copolymer. As used herein, "amphiphilic" refers to a molecule with both hydrophobic and hydrophilic properties. It is to be understood that the hydrophilic section of the block copolymer can connect to a targeting polypeptide of the invention, e.g., CRPPR. If the heart targeting molecule is to be used in conjunction with a nanoparticle, then the hydrophobic section of the block copolymer can be inserted into a nanoparticle membrane, thereby providing a heart targeting nanoparticle, as described above.

In various aspects, the peptide group has binding affinity for heart vein cells, heart capillary cells, heart artery cells or heart endothelial cells.

In various aspects, a PEG group connects the lipophilic moiety to the peptide group.

In various aspects, the peptide group includes more than one cysteine-arginine-proline-proline-arginine polypeptide where each polypeptide unit can be linked to another polypeptide unit by aminohexanoic acid, as described above.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A composition comprising:
    a plurality of nanoparticles;
    a bioactive agent encapsulated within, adhered to a surface of or integrated into the structure of the nanoparticles;
    a peptide group comprising a cysteine-arginine-proline-proline-arginine polypeptide, a peptidomimetic thereof or a homolog thereof;
    a lipophilic moiety connected to the peptide group by a poly(ethylene glycol) group, wherein the lipophilic moiety is inserted into the nanoparticle membrane to anchor the peptide group to the nanoparticle; and
    a poly(ethylene glycol) group operatively coupled to the surface of the nanoparticle.

2. The composition according to claim 1, wherein the peptide group has binding affinity for heart vein cells, heart capillary cells, heart artery cells or heart endothelial cells.

3. The composition according to claim 1, wherein the lipophilic moiety comprises an oleyl group.

4. The composition according to claim 1, wherein the poly(ethylene glycol) group connecting the lipohilic moiety to the peptide group comprises less than 100 ethylene glycol repeats.

5. The composition according to claim 4, wherein the poly(ethylene glycol) group connecting the lipohilic moiety to the peptide group comprises less than 75 ethylene glycol repeats.

6. The composition according to claim 5, wherein the poly(ethylene glycol) group connecting the lipohilic moiety to the peptide group comprises less than 50 ethylene glycol repeats.

7. The composition according to claim 6, wherein the poly(ethylene glycol) group connecting the lipohilic moiety to the peptide group comprises less than 25 ethylene glycol repeats.

8. The composition according to claim 1, wherein the peptide group comprises more than one cysteine-arginine-proline-proline-arginine polypeptide linked together by aminohexanoic acid.

9. The composition according to claim 1, wherein the bioactive agent is selected from the group consisting of an anti-stenosis agent, an anti-inflammatory agent, an antiplatelet, an anticoagulant, an antifibrin, an antithrombin, a cardioprotective agent, a cholesterol-lowering agent, aspirin, an angiotensin-converting enzyme, a beta blocker, a calcium channel blocker, nitroglycerin, a long-acting nitrate, a glycoprotein IIb-IIIa inhibitor or any combination thereof.

10. The composition according to claim 1, wherein the nanoparticles comprise liposomes, polymersomes or polymer particles.

11. A method for treating or preventing a disease comprising:
    providing a composition according to claim 1; and
    administering a therapeutically effective amount of the composition to a patient in need thereof.

12. The method according to claim 11, wherein administering the composition comprises intraarterial delivery.

13. The method according to claim 12, wherein intraarterial delivery comprises percutaneous transluminal coronary arterial delivery.

14. The method according to claim 12, wherein intraarterial delivery comprises using a catheter.

15. The method according to claim 11, wherein the disease is a vascular disease selected from the group consisting of atherosclerosis, stenosis, vulnerable plaque and heart failure.

* * * * *